United States Patent [19]

Shope

[11] Patent Number: 4,841,151
[45] Date of Patent: Jun. 20, 1989

[54] VARIABLE VOLUME FLOW CELL

[75] Inventor: William H. Shope, Santa Ana, Calif.

[73] Assignee: Beckman Instruments, Inc., Fullerton, Calif.

[21] Appl. No.: 14,738

[22] Filed: Feb. 13, 1987

[51] Int. Cl.$^4$ .................. G01T 1/20; G01N 23/12
[52] U.S. Cl. ..................... 250/364; 250/432 R; 242/47; 356/244
[58] Field of Search .............. 250/364, 428, 432 R; 356/244; 242/47.01, 47, 86, 7.21, 7.22

[56] References Cited

U.S. PATENT DOCUMENTS 3,597,611 8/1971 Harman .......................... 250/364
4,027,157 5/1977 Gervé et al. .................... 250/364

FOREIGN PATENT DOCUMENTS 3233543 3/1984 Fed. Rep. of Germany ........ 242/86

OTHER PUBLICATIONS

Sear, H., "A Method of Presenting Liquid Samples to the Flat Surface of a Scintillation Crystal", *Nucleonics*, Apr. 1953, pp. 52–53.
Berthold, Radioactivity Monitor LB 5025-HP, A Technical Description from Berthold Laboratorium, Germany.

*Primary Examiner*—Janice A. Howell
*Assistant Examiner*—William F. Rauchholz
*Attorney, Agent, or Firm*—William H. May; Paul R. Harder

[57] ABSTRACT

A flow cell for liquid scintillation counting having a spool wound with a length of light transparent tubing provides a variable volume of sample solution for analysis by selectively winding the spool with a select length of tubing, thus controlling sensitivity of anaysis and maintaining resolution of separated constituents in the sample. The flow cell comprises a spool rotatably held within a framework and which may be covered with a transparent material.

10 Claims, 2 Drawing Sheets

VARIABLE VOLUME FLOW CELL

FIELD OF INVENTION

The invention relates to liquid scintillation counters generally and in particular to flow cells for continuous flow type scintillation counters.

BACKGROUND OF THE INVENTION

In the art of liquid scintillation counting of a flowing sample, particularly where a sample material is subjected to liquid chromatography prior to analysis in a liquid scintillation counter, the liquid scintillation instrument generally utilizes an apparatus through which a sample solution including scintillation cocktail is flowed in proximity to a light detector. Such an apparatus through which the sample is flowed is generally referred to as a flow cell. Each of the separated bands in the sample solution emit a characteristic light emission due to the scintillation cocktail, which passes through a transparent portion of the flow cell to the photodetector to be detected. The information obtained from a detected light provides analysis of the sample.

Typically, a flow cell comprises a length of transparent tubing which is permanently arranged in a coil-like fashion such that light emissions from the sample solution flowing therethrough are concentrated to be received and detected by the photodetector. The tubing is selected having a small diameter to maintain sample resolution with a select length to provide a fixed volume of sample solution contained therein having exposure of the photodetector. The chosen length of tubing determines the volume of fluid contained within the flow cell exposed to the photodetector.

While the diameter of the transparent tubing is generally maintained consistent, varying lengths of tubing are utilized to provide differing volumes of sample solution for exposure to the photodetector. A greater volume of sample solution generally provides greater sensitivity in the detection of light, i.e. radioactivity in the sample solution by the scintillation instrument. Thus, in a constant flow system use of a longer length of tubing permits a given volume of fluid to be exposed to the photodetector for a longer period of time as it flows through the tubing permitting a longer term of measurement. This longer exposure period improves sensitivity. However a longer length of tubing providing a greater volume in the tubing coil of the flow cell has a disadvantage in that the separated bands of the sample solution which has been processed through liquid chromatography begin to diffuse and remix degrading resolution and accuracy of the analysis. Thus, depending on the sample material and the quality of separation in the sample solution, a large volume flow cell can be a disadvantage even though it may provide greater sensitivity.

Depending on the experiment to be performed an experimentor must select a flow cell having a volume which they believe is appropriate for the particular experiment, weighing the need of sensitivity in the detection of light versus the need of resolution in the chromatography for sample analysis. This selection may be different for each experiment and for each experimentor. Thus, a number of different fixed volume flow cells are generally made available to an experimentor for his selection and use. Such flow cells are for example manufactured and sold by Berthold Company of Wildbad, West Germany under Part Numbers Z-2000 and Z-4000.

The use of a number of different fixed volume flow cells however requires an experimentor to stock many different types in order to have them available so that they may have the freedom to select that specific volume flow cell which they deem appropriate for a given experiment. This can be expensive and often is troublesome in that it requires inventory space to maintain such a collection which could be used otherwise.

SUMMARY OF THE INVENTION

The invention presented herein is a flow cell for use in a liquid scintillation counter which permits the user to selectively determine the volume of sample solution contained therein. With this flow cell an experimentor may arbitrarily define the parameters of an experiment which they wish to perform. The flow cell comprises a spool on which a selected length of transparent tubing is wound. The selected length of tubing is provided access to a photodetector for analysis of the sample. By selecting the length of tubing to be wound on the spool in the flow cell, the volume of sample solution which is desired for exposure to the photodetector may be determined. The spool is mounted in a frame and preferably enclosed with a cover. Both may be transparent to permit light emissions from the sample solution to be examined.

By providing an apparatus which permits the experimentor to selectively determine the volume of sample material exposed for analysis, the experimentor has complete freedom to choose the sensitivity necessary for analysis in the particular experiment they wish to perform, while maintaining an adequate resolution in the individual bands defined in the sample solution by chromatography. This advantage overcomes the deficiencies found in prior art fixed volume flow cells.

DESCRIPTION OF THE PREFERRED EMBODIMENT

Figure 1:
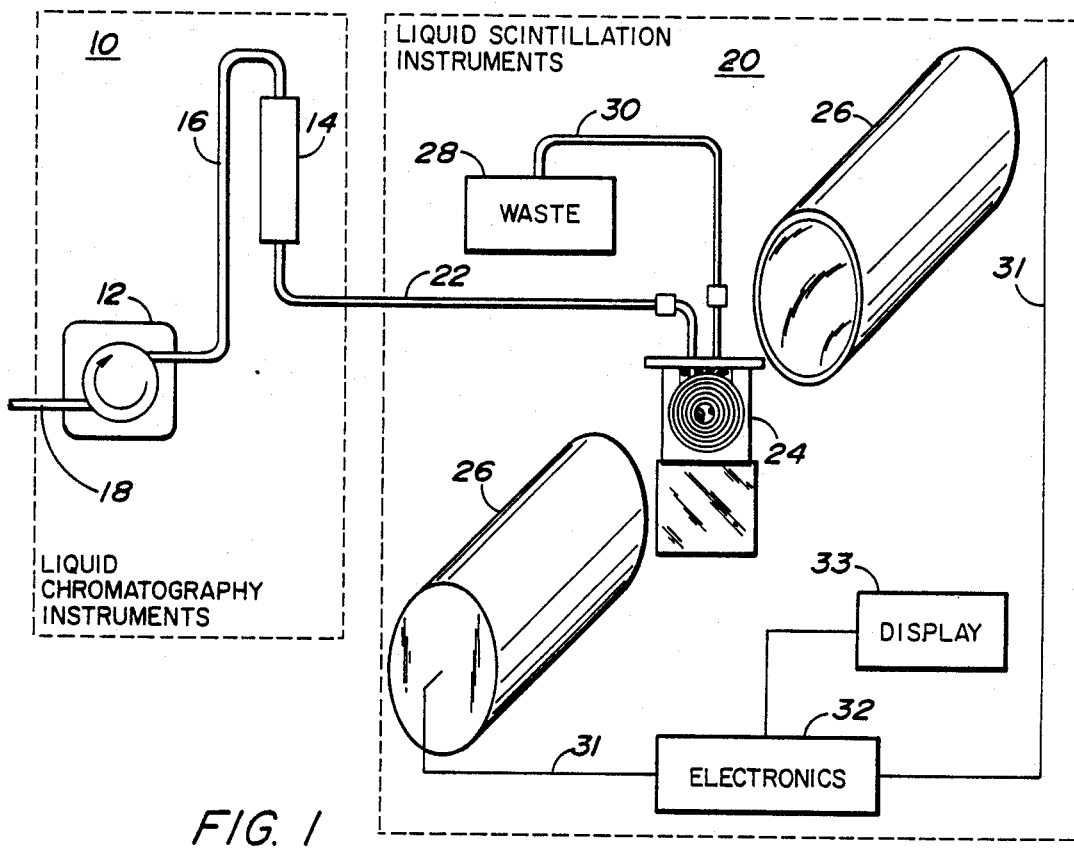
FIG. 1 is a schematic view of a liquid scintillation instrument with a liquid chromatography instrument utilizing the variable volume flow cell.

A liquid scintillation instrument for providing analysis of a sample substance containing a radioactive material, which has been separated through a liquid chromatography instrument, is depicted in FIG. 1. The liquid chromatography instrument 10 generally comprises of pump 12 which drives a sample material in solution through a chromatography column 14 under high pressure by way of tubing 16. The sample solution is obtained through input 18 to pump 12 from sample introducing apparatus generally known in the art of liquid chromatography instrumentation.

The separated sample is provided to liquid scintillation instrument 20 by way of line 22. The sample solution is directed through a variable volume flow cell 24 (shown in an opened position for clarity), which is positioned for exposure to photodetectors 26 to receive light emissions from the sample solution containing a scintillation cocktail. Preferably, the variable volume flow cell 24 is positioned such that a coil transparent tubing contained therein, as will be described as followed, is directed with greatest exposure to the photodetectors 26 for light transmission. This is generally a configuration in which the tubing coil of the flow cell 24 is wound in a plane parallel with the face of a photodetector 26. The sample solution which is flowed through the variable volume flow cell 24 is directed to a waste receptacle 28 through output line 30 following detection.

Light emissions detected from the sample solution containing a scintillation cocktail are received by the photodetectors 26 which provide an electrical signal through lines 31 to instrument electronics 32 of the liquid scintillation instrument for analysis. The electronics 32 provide a display 33 with information indicating a sample analysis for communication to an experimentor.

Figure 2:
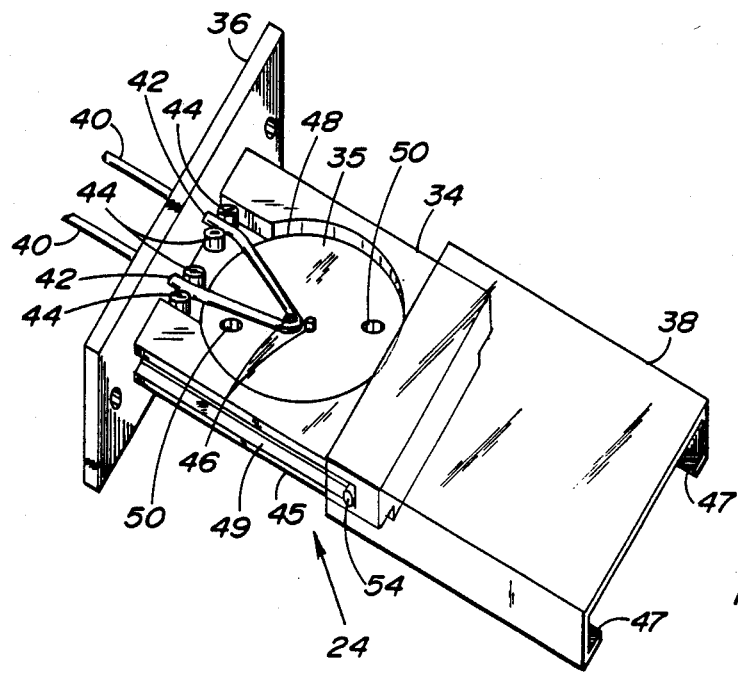
FIG. 2 is a view of a variable volume flow cell with transparent tubing inserted prior to winding the tubing on the spool.
Figure 3:
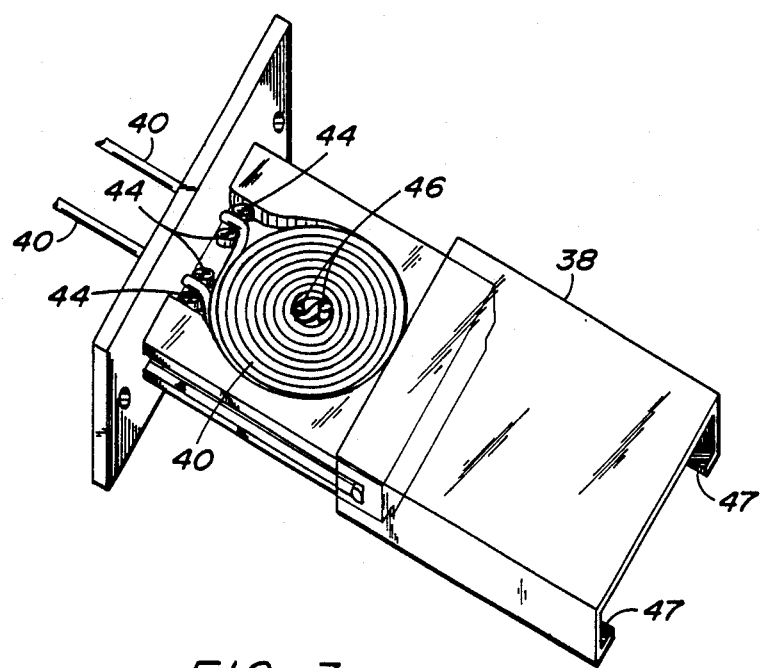
FIG. 3 is a view of a variable volume flow cell with tubing wound on the spool.
Figure 4:
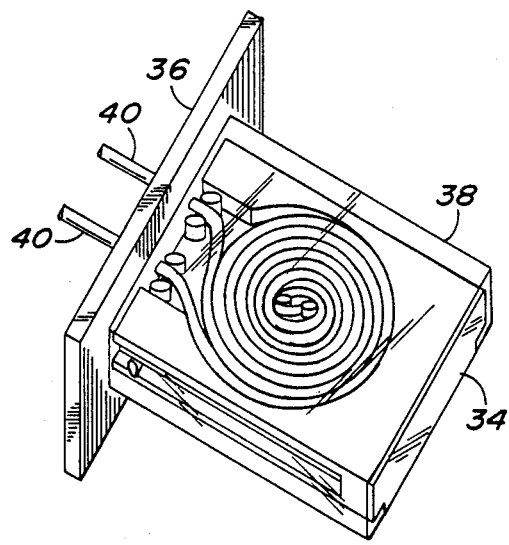
FIG. 4 is a view of a variable volume flow cell having a cover closed over the spool containing the wound transparent tubing and ready for use.

The variable volume flow cell which is the subject of this patent is depicted in FIGS. 2-4. Referring to FIG. 2, the variable volume flow cell 24 comprises a frame 34 which supports a spool 35 for rotational movement. The spool is supported in a circular opening through a central part of the frame 34 which has a step formed around the interior wall to receive spool 35. The frame 34 is attached to a mounting plate 36 by suitable fasteners (not shown) for assembly in a liquid scintillation instrument. Mounting plate 36 is utilized to position and hold the variable volume flow cell 24 within the liquid scintillation instrument. The frame 34 also mounts a cover 38 which is used to enclose the spool 35 when it is wound with the transparent tubing through which the sample material is flowed.

A translucent tube 40 made of a transparent fluorcarbon material such as teflon is cut to a desired length which provides a desired volume of sample material contained within the flow cell 24 when the tubing is wound around spool 35. The tubing 40 is inserted through openings 42 through the mounting plate 36 with the ends of the tubing 40 directed outwardly from the flow cell 24. The tubing 40 is directed towards the spool 34 by studs 44 between which the tubing 40 passes as it enters into the flow cell 24.

After insertion through the mounting plate 36 the tubing 40 is drawn through the mounting plate 36 leaving only a small interior portion 48 of the tubing remaining within the flow cell 24. The ends of the tubing outside of the flow cell 24 are adjusted to be equal in length. The interior portion 48 of the tubing is positioned over one of two pins 46 positioned centrally on the spool 35. The pins 46 act to direct the tubing 40 in a convoluted fashion around the spool 35 as it is rotated within the frame 34 of the variable volume flow cell 24, as is shown in FIG. 3 where the spool 35 is wound with tubing 40.

Once the interior portion of the tubing 48 is positioned over a pin 46 of the spool 35, the cover 38 may be left open or may be closed as spool 35 is rotated within the frame 34 to wind the tubing thereupon until the entire selected length of tubing is taken up, leaving sufficient end portions remaining for connection to the liquid scintillation instrument 20. After closing the cover 38 the variable volume flow cell 24 is positioned within the instrument 20 for use and tubing 40 connected to respective lines 22 and 30 of the liquid scintillation instrument 20.

The spool 35 is preferably provided with a pair of bores 50 radially positioned from the pins 46 for attachment of a tool from the back side to assist in winding the tubing 40 by rotation of the spool 35 within the frame 34.

FIG. 3 depicts the variable volume flow cell 24 with the cover 38 open having tubing 40 wound on the spool 35. The studs 44 have directed the tubing in uniform convoluted fashion around the spool 35 as it was turned, with pins 46 having acted to pull the tubing 40 around the spool 35.

FIG. 4 shows the variable volume flow cell 24 prior to mounting within the liquid scintillation counter 20 with the cover 38 moved to a closed position in enclosing the spool 35 within the flow cell 24 with tubing 40 wound around the spool.

Referring again to FIG. 2, frame 34 is provided with longitudinal slots 45 on each logitudinal end to slidably fit with a lip 47 formed on the sides of the cover 38. The cover 38 is thus permitted to slide over the frame 34 to enclose the spool 35 holding the tubing 40.

Frame 34 is also preferably provided a longitudinal slot 49 on a longitudinal end which receives a pin 54 directed inwardly from the side of the cover 38 to guide sliding movement of the cover over the frame 34. The end of the slot 49 opposite of the mounting plate 36 is closed so that the cover 38 cannot be completely removed from the frame 34.

The frame 34 may also be provided with a spring biased detent or ball (not shown) which can be used to engage a notch formed on the interior of the cover 38 to hold the cover 38 in a closed position over the frame 34 and spool 35.

The frame 34, spool 35, cover 38 are constructed from a transparent material so that light emissions from the sample solution containing a scintillator material being passed through the transparent tubing 40 contained in the flow cell 24, may pass therethrough and be detected by photocells within the scintillation instrument. For instance, these parts may be constructed of translucent castic acrylic material as is generally made available by the Rohme and Haas Company or other manufacturers or suppliers of plastics.

I claim:

1. A variable volume flow cell for receiving a continuous fixed flow directly from a liquid chromatography instrument, comprising:

the cell as part of a liquid scintillation instrument to receive the fixed flow directly from the liquid chromatography instrument;

a frame rotatably mounting a spool upon which a selectable length of open-bored transparent flexible tubing is wound, the tubing being open-bored in the wound state, and the length of the tubing being selectable according to the desired volume of the fixed flow of a sample and a scintillation material through the tubing; the sample and scintillation material being directly fed from the liquid chromatography instrument into the wound tubing, the wound tubing being in proximity to a light detector within the liquid scintillation instrument.

2. The flow cell of claim 1 wherein said frame is constructed of a light transparent material.

3. The flow cell of claim 1 wherein said spool is constructed of a light transparent material.

4. The flow cell of claim 1 additionally comprising a cover which encloses the spool wound with transparent tubing.

5. The flow cell of claim 4 wherein said cover is constructed of a light transparent material.

6. The flow cell of claim 4 wherein said cover is slidably mounted on said frame to slide over said spool as it is moved to a closed position.

7. A variable volume flow cell for a continuous flow liquid scintillation instrument comprising:

a light transparent frame having means for rotatably mounting a spool thereupon, means for mechanically guiding flexible tubing from an entry space across said frame to said spool and means for mounting a cover thereto;

the spool being rotatably mounted on said frame by said mounting means, said spool having a pair of pins centrally located thereupon for engaging the flexible tubing and winding said tubing over the face of said spool to permit winding from the center outwardly when the spool is rotated so as to vary the length of open-bored wound tubing according to the desired volume of a fixed flow of sample and scintillation material to flow in proximity of a light detector; and a light transparent cover movably mounted to said frame for covering said spool when it is wound with flexible tubing.

8. A variable volume flow cell for a continuous flow liquid scintillation instrument comprising a rotatable spool wound with a selectable length of transparent open-bored flexible tubing, the number of windings of the tubing being variable according to the desired volume of flow in proximity to a light detector, the wound open-bored tubing being rotatably held within a frame and enclosed within a cover, said flow cell being positioned within a liquid scintillation instrument in proximity to the light detector for transmitting light energy from a sample solution with scintillation material through said tubing to said light detector.

9. A variable volume flow cell for a continuous flow liquid scintillation instrument comprising open-bored coils of transparent flexible tubing, the number of coils of the tubing being selectable; and a body for supporting said tubing including means for drawing said tubing into said body in a selected number of coils to display a desired volume of sample material and scintillation material continuously flowing in said tubing to light detector in said liquid scintillation instrument.

10. A method for counting a variable selected volume of a sample solution and a scintillation material in a liquid scintillation counter, comprising:

(a) rotatably mounting a spool on a frame;

(b) passing a flexible open-bored tubing over a face of said spool, the spool having a pair of spaced pins substantially centrally located on the spool;

(c) looping the open-bored tubing over at least one pin;

(d) turning the spool to wind automatically a selected length of the tubing over the face of the spool starting from the center of the spool and about the pins;

(e) winding the tubing increasingly outwardly to add windings and to increase the volume of the tubing over the spool face, the tubing entering and exiting the spool in the same plane and in the same direction relative to the spool;

(f) passing a fixed flow of a sample material and a scintillation material through the tubing, such that the number of windings determines the desired volume of flow through the windings on the spool; and (g) displaying the selected volume of sample and scintillation material in the tubing to a light detector in a liquid scintillation instrument.

* * * * *